United States Patent [19]

Sidall et al.

[11] Patent Number: 4,741,326

[45] Date of Patent: May 3, 1988

[54] ENDOSCOPE DISPOSABLE SHEATH

[75] Inventors: Christopher O. R. Sidall, Rye; Robert L. Savitt, White Plains, all of N.Y.

[73] Assignee: Fujinon, Inc., Wayne, N.J.

[21] Appl. No.: 914,730

[22] Filed: Oct. 1, 1986

[51] Int. Cl.⁴ .............................................. A61B 1/00
[52] U.S. Cl. ........................................................ 128/4
[58] Field of Search ...................... 128/3, 4, 5, 6, 7, 8, 128/23

[56] References Cited

U.S. PATENT DOCUMENTS

| | | | |
|---|---|---|---|
| 3,417,746 | 12/1968 | Moore et al. | 128/6 |
| 3,581,738 | 6/1971 | Moore | 128/6 |
| 3,794,091 | 2/1974 | Ersek et al. | 128/6 X |
| 3,809,072 | 5/1974 | Ersek et al. | 128/23 |
| 4,195,624 | 4/1980 | Douglas | 128/8 |
| 4,201,199 | 5/1980 | Smith | 128/7 |
| 4,209,228 | 6/1980 | Chikama | |
| 4,408,692 | 10/1983 | Sigel et al. | |
| 4,646,722 | 3/1987 | Silverstein et al. | 128/4 |

Primary Examiner—William H. Grieb
Attorney, Agent, or Firm—Marks Murase & White

[57] ABSTRACT

A protective sheath assembly for use with a medical instrument is disclosed. The assembly comprises an elongatable hollow sheath attached to a transparent distal end plate. A tube extends from the end plate and is surrounded by the sheath. In order to provide for suctioning or irrigation of bodily cavities, a biopsy valve or other instrument is accommodated in the tube. An air or water channel may be provided for passing cleaning media over the transparent end plate, and nozzles can be embedded in the end plate to direct the cleaning media onto the end plate.

22 Claims, 3 Drawing Sheets

ENDOSCOPE DISPOSABLE SHEATH

BACKGROUND OF THE INVENTION

1. Field of the Invention

The present invention relates to a protective sheath assembly for use with endoscopes, sigmoidoscopes, and other surgical illuminating devices. The sheath is disposable and can be discarded after each use of the endoscope or similar surgical illuminating instrument.

2. Description of Related Art

Endoscopes are generally used for observing inside bodily cavities through an illuminating object. One such endoscope is shown in U.S. Pat. No. 3,581,738 to Moore. The device disclosed therein comprises an elongated tubular element which is to be received in a bodily cavity. The tubular element contains optical fibers for transmitting light between the inside of the the bodily cavity and an eyepiece at the viewing end of the endoscope. As endoscopes are used for examining bodily cavities, it is considered necessary to sterilize these devices after each use.

One way to avoid having to sterilize the endoscope is to provide a sheath which protects the endoscope. A sterile sheath for a surgical illuminator is disclosed in U.S. Pat. No. 3,794,091 to Ersek et al. The sheath taught by Ersek et al comprises a tubular portion terminating in a pointed transparent tip. A severe drawback of the Ersek et al device is that it does not permit any communication at all between the cavity wall and the endoscope. Thus, it is not possible to perform biopsy functions and the like with an endoscope having such a sheath. Further, the pointed tip is not conducive to spray cleaning and similar operations which improve the visability of the endoscope while in use.

U.S. Pat. No. 3,417,746 to Moore et al discloses a disposable endoscope. Since the endoscope is used only once there is no need to sterilize it. Having to provide a new endoscope with each use, however, nonetheless incurs large costs.

U.S. Pat. No. 4,195,624 to Douglas discloses a tubular sheath to facilitate insertion of an endoscope. It is similar to the Ersek et al device, in that the sheath does not permit communication between a cavity and the endoscope, nor does it provide an endpiece which can be easily cleaned during use.

U.S. Pat. No. 4,201,199 to Smith discloses a glass tube having a bulbous end structure which fits over the shaft of an endoscope. The glass tubing is integrally formed as one unitary piece, with the bulbous end fitting over the terminal point of the endoscope. The end piece cannot be spray cleaned while in use, and the device does not permit communication between the endoscope and cavity in any manner.

As noted, none of the devices just described permits communication, i.e., the transfer of fluid or material between the endoscope and the body cavity being inspected. It is often desirable, however, that such communication be permitted. For example, the endoscope operator may wish to insufflate the cavity with air or some other gas, or irrigate it with water or another liquid. The operator may also or alternatively wish to remove material from the cavity by suction or forceps carried by the endoscope. The devices just discussed, however, have no provision for accomplishing these tasks, which of course makes them unsuitable when it is desired that these tasks be performed.

SUMMARY OF THE INVENTION

It is an object of the invention to provide a disposable protection device compatible with all endoscopes which eliminates the need for sterilization, while at the same time permits communication between the body cavity and the endoscope. The use of the disposable protection device prevents contamination from such diseases as acquired immune deficiency syndrome (AIDS), hepatitis, and other communicable diseases.

This object is achieved by providing a covering device which is compatible with many different types of endoscopes. The structure comprises an elongated sheath which is adapted to receive the shaft of the endoscope. The sheath is attached at a first end to a distal end plate. A pipe extends from the distal end plate and is surrounded by the sheath. The pipe is provided for communicating with the endoscope device.

It is possible to provide nozzles in the distal end plate so that the end plate can be sprayed with fluid or air, thereby improving viewing accuracy during examination. Alternatively, the nozzle can be provided with cleaning channels extending down from the distal end plate and adapted to meet with an air or water supply.

DETAILED DESCRIPTION OF THE PREFERRED EMBODIMENTS

Figure 1:
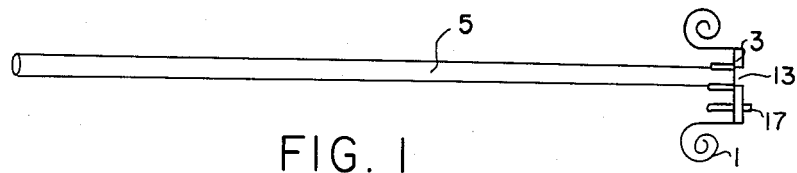
FIG. 1 illustrates a cross-sectional view of a first embodiment of the protective covering device; of the protective covering device.

Referring to FIG. 1, a first embodiment of a protective covering device in accordance with the invention is shown. An elongatable covering sheath means 1 is connected to a distal end plate 3. The distal end plate 3 is preferably made of a transparent material such as clear acrylic glass or plastic material. Other transparent materials may also be employed. A tube means 5 extends leftwardly in FIG. 1 from the distal end plate 3. The tube 5 can be made of plastic, PTFE, or other materials and is dimensioned such that it will easily slide up the forceps channel of an endoscope. The tube 5 and sheath 1 are preferably bonded to the distal end plate 3. Other methods of attachment may be used, as long as the tube 5 and sheath 1 are secured to the distal plate. An optically pure jelly can be applied to the surface of the distal end plate 3 to which the tube 5 and sheath 1 are bonded. Alternatively, jelly can be applied to the distal end of the endoscope prior to use of the protective device. The optically pure jelly insures an uninterrupted optical path.

The tube 5 is adapted to accommodate a biopsy valve or other instrument. A rubber valve 6 can be used to maintain the tube 5 in the appropriate position. In this manner, accessories can be suctioned and passed down the forceps channel.

Figure 2:
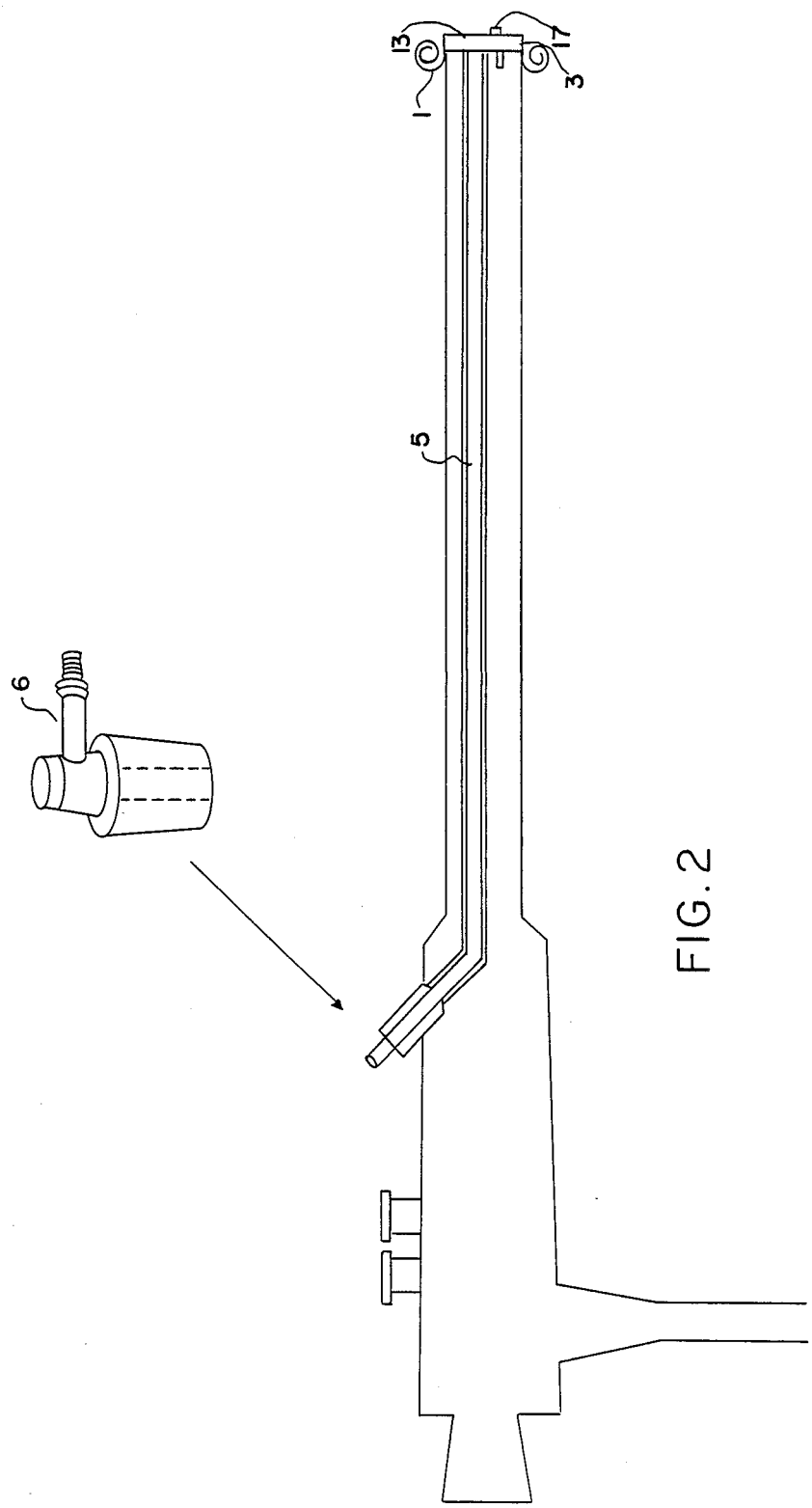
FIG. 2 illustrates a cross-sectional view of the first embodiment of the protective covering device in use with an endoscopic instrument.

The sheath 1 is ideally made of a flexible elastic material. As shown in FIGS. 1 and 2, the sheath 1 rolls up and rests near the distal end plate 3 in its normal rest position. The flexible elastic sheath 1 should be dimensioned so that its diameter in an unexpanded state is smaller than that of the endoscope shaft. This will ensure that the protective sheath 1 tightly and securely surrounds the endoscope shaft, thereby preventing contamination of the endoscope. The outside of the sheath 1 can be lubricated with a surgical lubricating jelly.

Figure 3:
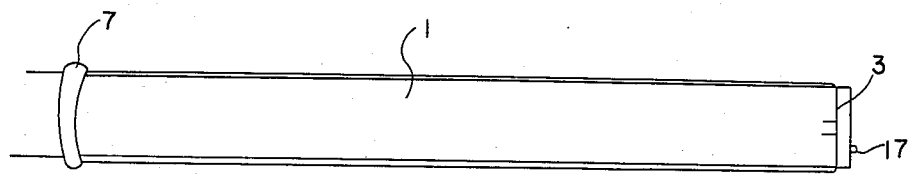
FIG. 3 illustrates a side elevation view of the protective covering device.

In order to maintain the elastic sheath in a rolled-down position, a securing means such as an elastic or rubber band 7 can be formed in the lower end of the sheath 1, as shown in FIG. 3. The elastic band 7 should be smaller in diameter than the sheath 1. In this manner, the sheath 1 will be maintained wherever the rubber band 7 is positioned. Alternatively, a separate elastic collar may be provided for securing the sheath in a rolled-down position. The collar may be composed of any material which will provide sufficient force to maintain the sheath 1 in position.

Figure 4:
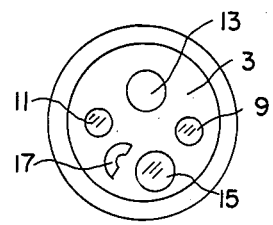
FIG. 4 illustrates a plan view of the distal plate of the protective covering device.

Referring to FIG. 4, a plan view of the distal end plate 3 is shown. Light guides 9 and 11 are aligned with optical fibers in the endoscope shaft. Light travels from a light source in the endoscope through the optical fibers to the light guides 9 and 11. The light guides 9 and 11 direct the light onto the viewing area of the bodily cavity or area to be inspected.

An opening 13 defines the perimeter of the forceps channel. A forceps or other instrument extends down the forceps channel and through opening 13 in order to contact the bodily cavity for performing biopsy or other similar functions. The distal end plate 3 also has an image guide lens 15 which transmits an image of the bodily cavity to an eyepiece of the endoscope. The image guide lens 15 is positioned so as to align with optical fibers for transmitting the image down the shaft of the endoscope. Also, the distal end plate 3 preferably has at least one nozzle means 17 with an associated nozzle opening for directing air, water or other cleaning media onto the outer surface of the image guide lens 15. Water or air passes through an air/water pipe, through the nozzle opening, and is directed onto the image guide lens 15 by the nozzle 17. Generally, an endoscope will be provided with pipes which spray fluid or air. The nozzle 17 is designed to mate with the air-water pipe of an endoscope so that the imaging area of the distal end plate 2 can be cleaned while in use. A rubber sealing means (not shown) is provided on the end of the nozzle 17 in order to form a seal with the pipe of the endoscope instrument. It is also possible to employ more than one nozzle 17.

Figure 5:
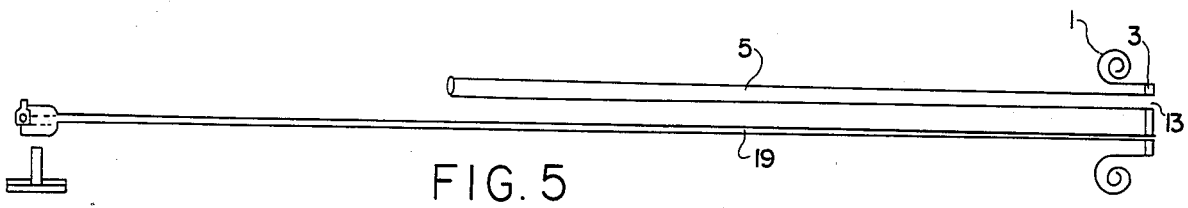
FIG. 5 illustrates an alternative embodiment of the protective covering device.

An alternative embodiment of the protective covering device is shown in FIG. 5. In FIG. 5, an air or water channel 19 is bonded to the distal end plate 3. The air-water channel 19 is positioned such that it remains outside of the forceps channel of the endoscope shaft, while remaining within the confines of the protective sheath 1. The air-water channel 19 is fitted into one of the nozzles 17 contained on the distal end plate 3. The air-water channel 19 guides air or water up to the distal end plate 3 in order to clean the surface thereof and improve viewing. The air-water channel 19 is designed so as to accommodate a syringe at the free end thereof. Alternatively, the free end of the air-water channel 19 can be fitted to an appropriate section of the control area of the endoscope instrument.

Figure 6:
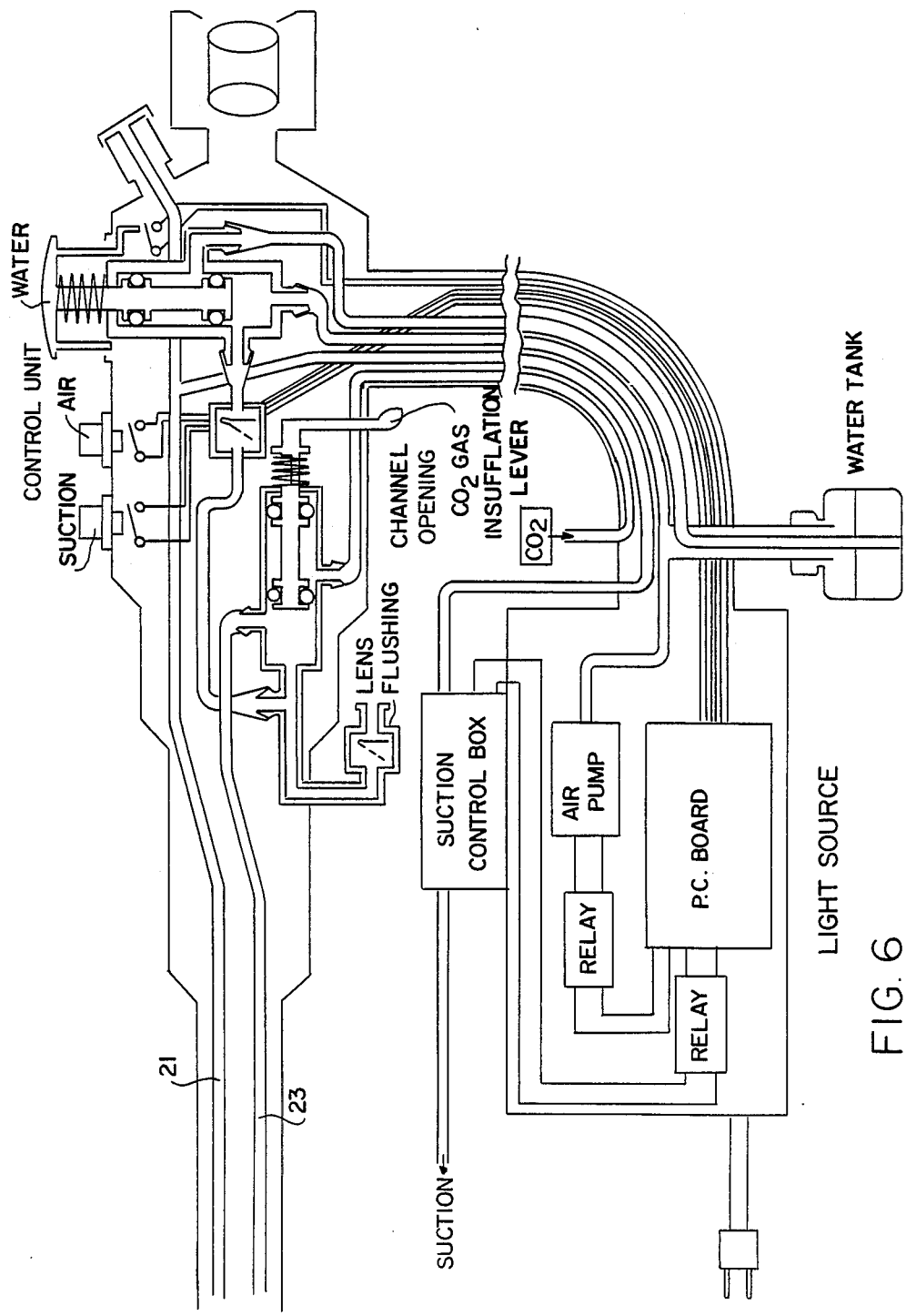
FIG. 6 illustrates a cross-sectional view of an endoscope for use with a protective sheath according to the invention.

FIG. 6 illustrates an endoscope for use with the protective sheath. The tube 5 of the protective sheath accommodates the suction tube 21 of the endoscope. Alternatively, a forceps instrument can be extended through the tube 5 of the sheath device.

An air or water channel 23 provided in the endoscope aligns with the nozzles 17 in the distal end plate 3, as discussed above.

As will be apparent to those familiar with the art, various modifications to the preferred embodiments may be effected without departing from the sprit and scope of the invention. The embodiments disclosed are illustrative rather than restrictive of the scope of the invention. For example, while a cylindrical sheath and circular end plate have been shown, it will be evident that these elements can be modified to any shape in order to accommodate various endoscopes. Furthermore, while the protective covering device has been shown as an integral unit, it may be possible to provide detachable parts which may be assembled to comprise a covering device in accordance with the invention.

What is claimed is:

1. A protective covering assembly for a medical instrument comprising:
an end plate having an opening therethrough;
an elongatable hollow sheath means for receiving a shaft, said sheath means being attached at a first end to said end plate; and
a tube means for accommodatng a medical instrument component attached at a first end to said end plate and aligned with said opening, said tube means being dimensioned to be received within a medical instrument channel and being surrounded by said sheath means.

2. The device of claim 1, further comprising:
a nozzle means disposed in said end plate for directing fluid onto said end palte.

3. The device of claim 2, further comprising:
a channel extending substantially parallel to said tube means and connected at a first end to said nozzle means.

4. The assembly according to claim 3, further comprising a fastening means disposed at a second end of said channel for fastening said channel to an accessory element.

5. The assembly according to claim 4, wherein said fastening means is adapted to engage a syringe.

6. The assembly according to claim 2, further comprising a sealing means disposed on said nozzle means.

7. The assembly according to claim 1, wherein said sheath means is comprised of an elastic material.

8. The assembly according to claim 7, wherein a diameter of said sheath means in an unexpanded state is smaller than a diameter of the shaft.

9. The assembly according to claim 1, wherein said sheath means is comprised of a flexible material.

10. The assembly according to claim 9, wherein said sheath means rests in a rolled up position forming a substantially ring-shaped element, and further comprising:
a securing means for securing a second end of said sheath means to the shaft in an unrolled position.

11. The assembly according to claim 10, wherein said securing means is an elastic collar adapted to grip said sheath means around the shaft.

12. The assembly according to claim 10, wherein said securing means is integrally formed with said sheath means.

13. The assembly according to claim 1, wherein said sheath is comprised of rubber.

14. The assembly of claim 1, wherein said end plate is comprised of a substantially transparent material.

15. The assembly of claim 1, wherein said tube means is comprised of plastic.

16. The assembly of claim 1, wherein said end plate comprises:
   an image lens means for transmitting an image to the instrument; and
   a light guide means for illuminating an image area.

17. The assembly of claim 16, further comprising a nozzle means for directing a cleansing medium onto said image lens.

18. The assembly of claim 1, wherein said sheath means is secured at said first end around a periphery of said end plate.

19. The assembly of claim 18, wherein said tube means is secured at its outer periphery to said end plate.

20. An assembly for covering a probe of a medical instrument, said assembly comprising:
   an end plate adjacent an end of said probe and defining an opening;
   a sheath secured at one end around a rim of said end plate and adapted to be elongatable to seal along an outer surface of said probe when said probe end is adjacent said end plate;
   tube means secured to said end plate at said opening and dimensioned to be received within a channel of the medical instrument; and
   means in said end plate for permitting light to pass therethrough.

21. An assembly as claimed in claim 20, further comprising a nozzle means disposed in said end plate for directing fluid onto said end plate.

22. An assembly as claimed in claim 21, further comprising a channel extending from said end plate and connected at a first end to said nozzle means.

* * * * *